United States Patent
Lang et al.

(10) Patent No.: US 8,372,993 B2
(45) Date of Patent: Feb. 12, 2013

(54) METHOD FOR SEPARATING TRIOXANE FROM A TRIOXANE/FORMALDEHYDE/WATER MIXTURE BY MEANS OF PRESSURE CHANGE RECTIFICATION

(75) Inventors: Neven Lang, Mannheim (DE); Joachim Thiel, Neustadt (DE); Eckhard Stroefer, Mannheim (DE); Julia Kirschbaum, Markgröningen (DE); Markus Siegert, Heidelberg (DE)

(73) Assignee: BASF SE, Ludwigshafen (DE)

( * ) Notice: Subject to any disclaimer, the term of this patent is extended or adjusted under 35 U.S.C. 154(b) by 569 days.

(21) Appl. No.: 12/523,741

(22) PCT Filed: Jan. 23, 2008

(86) PCT No.: PCT/EP2008/050745
§ 371 (c)(1),
(2), (4) Date: Nov. 30, 2009

(87) PCT Pub. No.: WO2008/090169
PCT Pub. Date: Jul. 31, 2008

(65) Prior Publication Data
US 2010/0121081 A1   May 13, 2010

(30) Foreign Application Priority Data
Jan. 25, 2007 (EP) .................................. 07101198

(51) Int. Cl.
*C07D 309/00* (2006.01)
(52) U.S. Cl. ............ 549/368; 568/449; 203/74; 203/14; 203/17; 203/75; 203/77; 203/78; 203/80
(58) Field of Classification Search ................. 549/368; 568/449; 203/74, 14, 17, 75, 77, 78, 80
See application file for complete search history.

(56) References Cited

U.S. PATENT DOCUMENTS

| 5,766,424 A | * | 6/1998 | Arnold et al. ................... 203/74 |
| 6,200,429 B1 | | 3/2001 | Freyhof et al. |
| 6,610,888 B1 | | 8/2003 | Stroefer et al. |
| 7,713,387 B2 | * | 5/2010 | Siegert et al. ................... 203/74 |
| 2007/0155972 A1 | | 7/2007 | Lang et al. |
| 2007/0272540 A1 | | 11/2007 | Siegert et al. |

FOREIGN PATENT DOCUMENTS

| DE | 1668867 | 12/1971 |
| DE | 19732291 A1 | 1/1999 |
| DE | 19925870 A1 | 12/2000 |
| WO | WO-2005/063353 A1 | 7/2005 |
| WO | WO-2005/063733 A1 | 7/2005 |

* cited by examiner

*Primary Examiner* — Noble Jarrell
*Assistant Examiner* — Raymond Covington
(74) *Attorney, Agent, or Firm* — Connolly Bove Lodge & Hutz LLP

(57) ABSTRACT

A process for removing trioxane from a use stream I of formaldehyde, trioxane and water, by
a) providing a use stream I which comprises formaldehyde as the main component and trioxane and water as the secondary components,
b) feeding the use stream I, a recycle stream V and a recycle stream VII which comprises formaldehyde as the main component and water and trioxane as the secondary components into a first distillation stage and distilling to obtain a stream II a steam III and formaldehyde as the and a steam X
c) distilling the stream III, in a second distillation stage the pressure in the second distillation stage being from 0.1 to 15 bar higher than the pressure in the first distillation stage, to obtain a stream IV and the recycle stream V as the secondary components,
d) feeding the stream X and if appropriate a stream IX into a third distillation stage and distilling at a pressure of from 1 to 10 bar to obtain a stream VI which consists substantially of water and a recycle stream VII which comprises formaldehyde as the main component and water and trioxane as the secondary components.

17 Claims, 1 Drawing Sheet

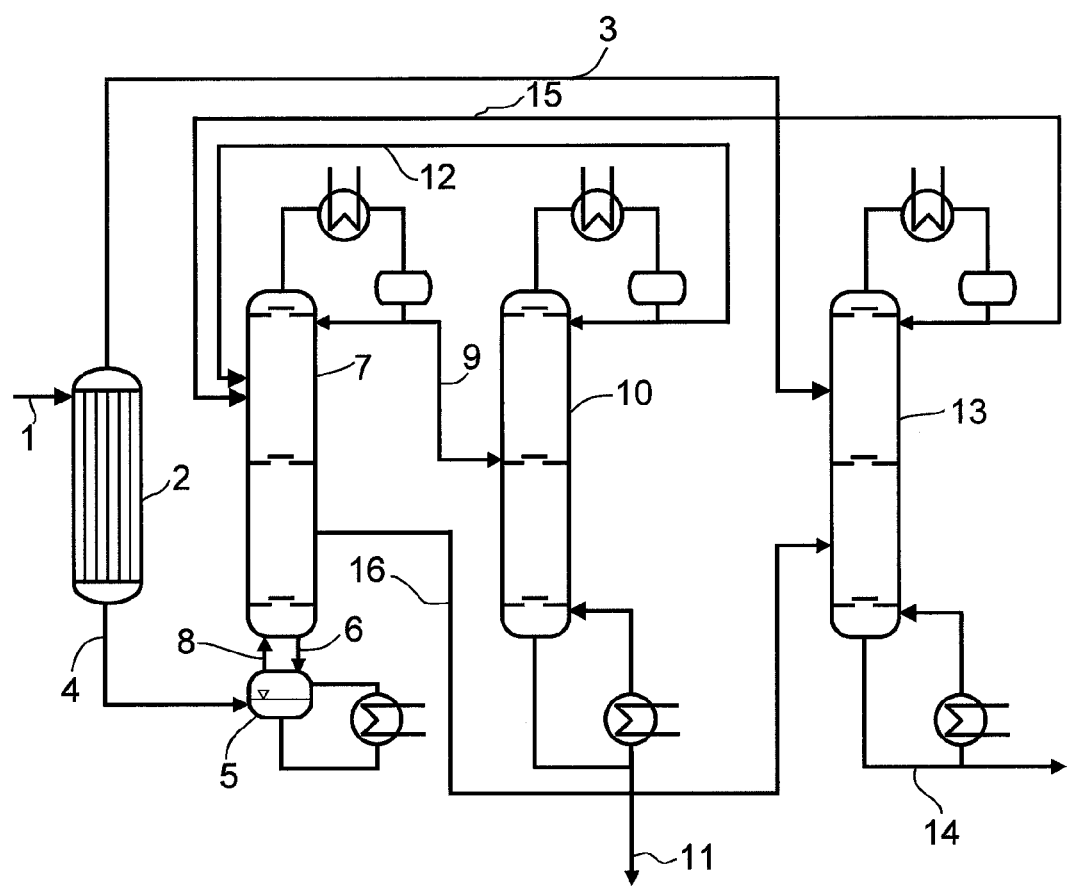

METHOD FOR SEPARATING TRIOXANE FROM A TRIOXANE/FORMALDEHYDE/WATER MIXTURE BY MEANS OF PRESSURE CHANGE RECTIFICATION

RELATED APPLICATIONS

This application is a national stage application (under 35 U.S.C. §371) of PCT/EP2008/050745, filed Jan. 23, 2008, which claims benefit of European application 07101198.5, filed Jan. 25, 2007.

The invention relates to a process for removing trioxane from a trioxane/formaldehyde/water mixture, and also to a process for preparing trioxane.

Trioxane is generally prepared by distilling aqueous formaldehyde solution in the presence of acidic catalysts. The trioxane is subsequently removed from the distillate comprising formaldehyde and water by extraction with halogenated hydrocarbons such as methylene chloride or 1,2-dichloroethane, or other, water-immiscible solvents.

DE-A 1 668 867 describes a process for removing trioxane from mixtures comprising water, formaldehyde and trioxane by extraction with an organic solvent. In this process, an extraction section consisting of two subsections is charged at one end with a customary organic, virtually water-immiscible extractant for trioxane, and at the other end with water. Between the two subsections, the distillate of the trioxane synthesis to be separated is fed. On the side of the solvent feed, an aqueous formaldehyde solution is then obtained, and on the side of the water feed, a virtually formaldehyde-free solution of trioxane in the solvent. In one example, the distillate which is obtained in the trioxane synthesis and is composed of 40% by weight of water, 35% by weight of trioxane and 25% by weight of formaldehyde is metered into the middle section of a pulsation column, and methylene chloride is fed at the upper end of the column and water at the lower end of the column. In this case, an about 25% by weight solution of trioxane in methylene chloride is obtained at the lower end of the column and an about 30% by weight aqueous formaldehyde solution at the upper end of the column.

A disadvantage of this procedure is the occurrence of extractant which has to be purified. Some of the extractants used are hazardous substances (T or T$^+$ substances in the context of the German Hazardous Substances Directive), whose handling entails special precautions.

DE-A 197 32 291 describes a process for removing trioxane from an aqueous mixture which consists substantially of trioxane, water and formaldehyde, by removing trioxane from the mixture by pervaporation and separating the trioxane-enriched permeate by rectification into trioxane and an azeotropic mixture of trioxane, water and formaldehyde. In the example, an aqueous mixture consisting of 40% by weight of trioxane, 40% by weight of water and 20% by weight of formaldehyde is separated in a first distillation column under atmospheric pressure into a water/formaldehyde mixture and into an azeotropic trioxane/water/formaldehyde mixture. The azeotropic mixture is passed into a pervaporation unit which comprises a membrane composed of polydimethylsiloxane with a hydrophobic zeolite. The trioxane-enriched mixture is separated in a second distillation column under atmospheric pressure into trioxane and, in turn, into an azeotropic mixture of trioxane, water and formaldehyde. This azeotropic mixture is recycled before the pervaporation stage.

A disadvantage of this procedure is the very high capital costs for the pervaporation unit.

It is an object of the invention to provide a process for removing trioxane from azeotropic trioxane/formaldehyde/water mixtures, which does not need any of the extraction steps or pervaporation steps of the prior art.

This object is achieved by a process for removing trioxane from a use stream I of formaldehyde, trioxane and water, by a) providing a use stream I which comprises formaldehyde as the main component and trioxane and water as the secondary components, b) feeding the use stream I, a recycle stream V and a recycle stream VII which comprises formaldehyde as the main component and water/trioxane as the secondary components into a first distillation stage and distilling at a pressure of from 0.1 to 2.5 bar to obtain a stream II which comprises formaldehyde as the main component and water as the secondary component, and a stream III which comprises trioxane as the main component and water and formaldehyde as the secondary components, and a stream X which comprises water, trioxane and formaldehyde, c) distilling the stream III, optionally after removing low boilers from the stream III in a low boiler removal stage, in a second distillation stage at a pressure of from 0.2 to 17.5 bar, the pressure in the second distillation stage being from 0.1 to 15 bar higher than the pressure in the first distillation stage, to obtain a stream IV which consists substantially of trioxane and the recycle stream V which comprises trioxane as the main component and water and formaldehyde as the secondary components, d) feeding the stream X and if appropriate a stream IX which comprises water as the main component into a third distillation stage and distilling at a pressure of from 1 to 10 bar to obtain a stream VI which consists substantially of water and a recycle stream VII which comprises formaldehyde and water and trioxane.

The main component is the component having the larger or largest proportion by mass in the mixture in question. The proportion by mass of the particular component in the main mixture is preferably at least 40% by weight. A stream "consists substantially of" one or more components, when it consists of at least 90% by weight of this or these components.

It is known that trioxane, formaldehyde and water form a ternary azeotrope which, at a pressure of 1 bar, has the composition of 69.5% by weight of trioxane, 5.4% by weight of formaldehyde and 25.1% by weight of water.

According to the invention, this azeotrope is circumvented by pressure swing distillation, in which a first and a second distillation are carried out at different pressures. In a first distillation column which is operated at lower pressure, the starting mixture Ia is separated into a trioxane/water mixture having low formaldehyde content III and a substantially trioxane-free formaldehyde/water mixture II. The formaldehyde/water mixture II may be recycled into the trioxane synthesis. In a further distillation column operated at higher pressure, the trioxane/formaldehyde/water mixture III obtained is separated into pure trioxane and a trioxane/formaldehyde/water mixture V having a lower trioxane content. The mixture V is recycled into the first distillation column. According to the invention, the side draw stream X also obtained in the first distillation column is a mixture having a high water content, from which, in a third distillation column, substantially pure water VI is removed and a trioxane/formaldehyde/water mixture a lower water content is obtained. This mixture VII is recycled into the first distillation column. Preferably, a water-containing stream IX which is obtained in the concentration of aqueous formaldehyde solution is likewise fed into the third distillation column.

Suitable distillation columns are any distillation columns such as packed or tray columns. These may comprise any internals, structured packings or random packings.

The pressure in the second distillation stage is from 0.1 to 15 bar higher than the pressure in the first distillation stage. This pressure differential is preferably from 1.0 to 10 bar, more preferably from 1.5 to 5 bar.

All pressure data relate to the pressure at the top of the particular column.

The first distillation stage is carried out at a pressure of from 0.1 to 2.5 bar, preferably from 0.25 to 1.5 bar. The first distillation stage is generally carried out in a distillation column having at least 2, preferably from 2 to 50, more preferably from 4 to 25, theoretical plates. In general, the stripping section of this column includes at least 25%, preferably from 50 to 90%, of the theoretical plates of this column.

The feed stream I generally comprises from 40 to 80% by weight of formaldehyde, from 20 to 59% by weight of water and from 1.0 to 30% by weight of trioxane. The feed stream I is preferably fed in vaporous form into the bottom of the first distillation column.

The stream II, which is generally obtained as a bottom draw stream of the first distillation column, generally comprises less than 5% by weight, preferably less than 2% by weight, of trioxane, more preferably less than 1% by weight of trioxane. For example, the composition of the stream II is as follows: from 55 to 85% by weight of formaldehyde, from 15 to 45% by weight of water and from 0 to 5% by weight of trioxane. The stream III, which is generally obtained as a top draw stream of the first distillation column, generally comprises more than 60% by weight, preferably more than 63% by weight, more preferably more than 65% by weight, of trioxane. For example, the composition of the stream III is as follows: from 3 to 20% by weight of formaldehyde, from 10 to 30% by weight of water and from 60 to 75% by weight of trioxane. The stream X, which is obtained as a side draw stream of the first distillation column, comprises water, formaldehyde and trioxane, water or formaldehyde generally being the main component. For example, the stream X has the following composition: from 10 to 50% by weight of formaldehyde, from 10 to 50% by weight of water and from 3 to 40% by weight of trioxane.

The stream II is preferably recycled into the trioxane synthesis.

The streams I, III, V and VII may also comprise up to 15% by weight of low boilers. Typical low boilers which can be formed in the trioxane synthesis and the subsequent distillative separation are methyl formate, methylal, dimethoxydimethyl ether, methanol, formic acid, and also further hemiacetals and full acetals. To remove these low boilers, a low boiler removal stage may optionally be carried out between the first and the second distillation stage. In this case, the low boilers are preferably removed via the top of a low boiler removal column which is generally operated at a pressure of from 0.1 to 5 bar, preferably at a pressure of from 1.0 to 2.5 bar. In general, the low boiler removal column has at least 2 theoretical plates, preferably from 15 to 50 theoretical plates. The stripping section of this column generally includes from 25 to 90%, preferably from 50 to 75%, of the theoretical plates of this column. The content of the components having a lower boiling point than trioxane in the bottom effluent of the low boiler removal column is generally less than 5% by weight, preferably less than 2.5% by weight, more preferably less than 1.5% by weight.

In general, a low boiler removal is carried out.

The stream III is separated in a second distillation stage at a pressure of from 0.2 to 17.5 bar into a stream IV composed of substantially pure trioxane and a stream V which comprises trioxane, as the main component and additionally water and formaldehyde. This second distillation stage is preferably carried out at from 2.5 to 10 bar. In general, this second distillation stage is carried out in a distillation column having at least 2 theoretical plates, preferably from 10 to 50 theoretical plates, and the stream IV is obtained as a bottom draw stream or as a side draw stream in the stripping section of the column, and the stream V is obtained as a top draw stream. In general, the stripping section of the distillation column includes from 25 to 90%, preferably from 50 to 75%, of the theoretical plates of this column.

In general, the stream IV comprises from 95 to 100% by weight, preferably from 99 to 100% by weight, of trioxane, and from 0 to 5% by weight, preferably from 0 to 1% by weight, of water and secondary components. Secondary components are in particular the abovementioned low boilers, but also components having a higher boiling point than trioxane. The content of water and secondary components in the trioxane stream IV is more preferably <0.1%. It may even be <0.01%. The stream V comprises, for example, from 5 to 20% by weight of formaldehyde, from 15 to 35% by weight of water and from 50 to 75% by weight of trioxane.

The stream X and if appropriate a water-containing stream IX are separated in a third distillation stage at a pressure of from 1 to 10 bar into a stream VI which comprises substantially water and a recycle stream VII which comprises trioxane as the main component and additionally water and formaldehyde. The water-containing stream IX is obtained if appropriate as a vapor draw stream of a formaldehyde concentration unit which is designed as an evaporator and comprises, for example, from 70 to 97% by weight of water and from 3 to 30% by weight of formaldehyde. Preference is given to carrying out the third distillation stage at a pressure of from 2.5 to 8 bar. In general, the third distillation stage is carried out in a distillation column having at least two theoretical plates, preferably from 10 to 50 theoretical plates, and the water stream VI is obtained as a bottom draw stream or as a side draw stream from the column and the recycle stream VII as a top draw stream. The stream X is preferably added in the upper region of the column, for example in the region of the uppermost third of the theoretical plates of the column, and the stream IX in the middle region of the column, for example in the region of the middle third of the theoretical plates of the column.

The water stream VI preferably consists of more than 95% by weight, more preferably of more than 97% by weight, of water. For example, the stream VI comprises from 98 to 100% by weight of water, from 0 to 1% by weight of formaldehyde and from 0 to 1% by weight of secondary components.

The stream VII comprises, for example, from 10 to 55% by weight of formaldehyde, from 5 to 50% by weight of water and from 5 to 55% by weight of trioxane.

The stream VII may be partly or fully recycled upstream of the first distillation stage; preference is given to recycling it substantially fully in the first distillation stage. It may be mixed there with the recycle stream V or fed separately from the latter to the first distillation column.

The present invention also provides a process for preparing trioxane from an aqueous formaldehyde solution, by preparing the use stream I comprising formaldehyde, trioxane and water from an aqueous formaldehyde solution in a preceding trioxane synthesis stage and subsequently removing trioxane from the stream I as described above. Alternatively, the trioxane synthesis and the first distillation stage may be combined in a reactive distillation.

In one embodiment of the process according to the invention, a stream XI composed of an aqueous formaldehyde solution of a preceding trioxane synthesis stage is fed and converted in the presence of acidic homogeneous or heterogeneous catalysts such as ion exchange resins, zeolites, sulfuric acid and p-toluenesulfonic acid at a temperature of generally from 70 to 130° C. Operation may be effected in a distillation column or an evaporator (reactive evaporator). The product mixture of trioxane/formaldehyde and water is then obtained as a vaporous vapor draw stream of the evaporator or as a top draw stream at the top of the column. The trioxane synthesis stage may also be carried out in a fixed bed or fluidized bed reactor over a heterogeneous catalyst, for example an ion exchange resin or zeolite.

In a further embodiment of the process according to the invention, the trioxane synthesis stage and the first distillation stage are carried out as a reactive distillation in one reaction column. This may comprise a fixed catalyst bed of a heterogeneous acidic catalyst in the stripping section. Alternatively, the reactive distillation may also be carried out in the presence of a homogeneous catalyst, in which case the acidic catalyst is present in the column bottom together with the aqueous formaldehyde solution.

In general, the aqueous formaldehyde solution which is fed to the trioxane synthesis stage comprises from 30 to 85% by weight of formaldehyde and from 15 to 70% by weight of water. This solution may be obtained in a preceding concentration step from an aqueous formaldehyde solution having low formaldehyde concentration. The concentration step may be carried out, for example, in an evaporator, preferably a falling-film evaporator.

The preceding concentration step may be carried out, for example, as described in DE-A 199 25 870.

In one embodiment of the process according to the invention, a stream VIII of an aqueous formaldehyde solution is concentrated in an evaporator, preferably a falling-film evaporator, to obtain the stream XI consisting of aqueous formaldehyde solution having a higher formaldehyde concentration. The vapor draw stream of the evaporator which is highly depleted in formaldehyde is fed into the third distillation stage as the aqueous stream IX. Stream VIII comprises, for example, from 40 to 60% by weight of formaldehyde and from 40 to 60% by weight of water. The concentrated stream XI comprises, for example, from 55 to 80% by weight of formaldehyde and from 20 to 45% by weight of water. The low formaldehyde vapor draw stream IX comprises, for example, from 10 to 25% by weight of formaldehyde and from 75 to 90% by weight of water.

The resulting pure trioxane, whose purity may be >99% by weight, >99.9% by weight or even >99.99% by weight, is preferably used to prepare polyoxymethylene (POM), polyoxymethylene derivatives such as polyoxymethylene dimethyl ether (POMDME) and diaminodiphenylmethane (MDA).

The invention is illustrated in detail hereinbelow with reference to the drawing.

FIG. 1 shows an example of an embodiment of the process according to the invention.

An aqueous formaldehyde solution 1 (stream VIII) is fed to the evaporator 2, for example a thin-film evaporator, falling-film evaporator or helical-tube evaporator. The vapor draw stream 3 (stream IX) of the evaporator which is obtained is a formaldehyde-depleted aqueous solution, the bottom draw stream 4 (stream XI) of the evaporator a formaldehyde-rich aqueous solution. The latter is fed with the formaldehyde-rich bottom draw stream 8 (stream II) of the first distillation column 7 to the trioxane synthesis reactor 5 which is configured as an evaporator. The vaporous trioxane/formaldehyde/water mixture 6 (stream I) leaving the trioxane synthesis reactor is fed to the bottom of the first distillation column 7. The trioxane-rich top draw stream 15 (stream VII) of the third distillation column 13 is fed to the distillation column 7 close to the top of the column. A formaldehyde/water stream 8 (steam II) is withdrawn from the distillation column 7 as bottom draw stream, a low-water formaldehyde/water/trioxane stream 9 (stream III) as a top draw stream and a water-rich formaldehyde/water/trioxane stream 16 as a side draw stream. Stream 8 is recycled into the reactor 5 together with the stream 4. The low-water formaldehyde/water/trioxane stream 9 is fed to the distillation column 10 and separated there into a bottom draw stream 11 (stream IV) composed substantially of pure trioxane and a top draw stream 12 (stream V) which comprises predominantly trioxane and additionally water and formaldehyde. The stream 12 is recycled into the first distillation column. The water-rich formaldehyde/water/trioxane steam 16 and the low-formaldehyde aqueous vapor draw stream 3 (stream IX) of the evaporator 2 are fed to the third distillation column and separated there into a stream 14 (stream VI) which consists substantially of water and is discharged, and the recycle stream 15 (stream VII) which comprises predominantly formaldehyde and additionally water and trioxane.

EXAMPLE

In the theoretical simulation of the process illustrated in the FIGURE, streams 4, 9, 11, 12, 3, 14, 15 and 16 of the compositions reported in the tables were obtained. The following parameters were selected: the first distillation stage is carried out at a pressure of 0.7 bar in a column 7 having 10 theoretical plates. The reflux ratio is 0.8, the top temperature 80° C. and the bottom temperature 94° C. The second distillation stage is carried out at a pressure of 4.0 bar in a column 10 having 40 theoretical plates. The reflux ratio is 0.5, the top temperature 146° C., and the bottom temperature 181° C. The feed 9 is disposed at the height of the 35th theoretical plate. The third distillation stage is carried out at a pressure of 6.0 bar in a column 13 having 10 theoretical plates. The reflux ratio is 1.5, the top temperature 146° C. and the bottom temperature 160° C. The feed 3 is disposed at the height of the 8th theoretical plate.

| | Stream | | | | | | | |
|---|---|---|---|---|---|---|---|---|
| | 4 (XI) | 9 (III) | 11 (IV) | 12 (V) | 3 (IX) | 14 (VI) | 15 (VII) | 16 (X) |
| Mass flow rate [kg/h] | 4.1 | 11.9 | 3 | 9.0 | 2.0 | 3.1 | 8.3 | 9.5 |
| Formaldehyde [% by wt.] | 65.0 | 8.5 | <1 | 11.3 | 15.3 | <1 | 52.2 | 42.7 |
| Water [% by wt.] | 35.0 | 21.5 | <1 | 28.7 | 84.7 | >99 | 22.6 | 35.2 |
| Trioxane [% by wt.] | 0 | 70.0 | >99 | 60.0 | 0 | 0 | 25.2 | 22.1 |

The invention claimed is:

1. A process for removing trioxane from a use stream I of formaldehyde, trioxane and water, by
   a) providing a use stream I which comprises formaldehyde as the main component and trioxane and water as the secondary components,
   b) feeding the use stream I, a recycle stream V which comprises trioxane as the main component and water and formaldehyde as the secondary components and a recycle stream VII which comprises formaldehyde as the main component and water and trioxane as the secondary components into a first distillation stage and distilling at a pressure of from 0.1 to 2.5 bar to obtain a stream II which comprises formaldehyde as the main component and water as the secondary component, and a stream III which comprises trioxane as the main component and water and formaldehyde as the secondary components, and a stream X which comprises water, trioxane and formaldehyde, c) distilling the stream III, optionally after removing low boilers from the stream III in a low boiler removal stage, in a second distillation stage at a pressure of from 0.2 to 17.5 bar, the pressure in the second distillation stage being from 0.1 to 15 bar higher than the pressure in the first distillation stage, to obtain a stream IV which consists substantially of trioxane and the recycle stream V which comprises trioxane as the main component and water and formaldehyde as the secondary components, d) feeding the stream X and optionally a stream IX which comprises water as the main component into a third distillation stage and distilling at a pressure of from 1 to 10 bar to obtain a stream VI which consists substantially of water and a recycle stream VII which comprises formaldehyde as the main component and water and trioxane as the secondary components.

2. The process according to claim 1, wherein the pressure in the second distillation stage is from 1.0 to 10 bar higher than the pressure in the first distillation stage.

3. The process according to claim 1, wherein the first distillation stage is carried out at a pressure of from 0.25 to 1.5 bar.

4. The process according to claim 1, wherein the third distillation stage is carried out at a pressure of from 2.5 to 8 bar.

5. The process according to claim 1, wherein the first distillation stage is carried out in a first distillation column having at least two theoretical plates, the second distillation stage in a second distillation column having at least 2 theoretical plates and the third distillation stage in a third distillation column having at least two theoretical plates.

6. The process according to claim 5, wherein the stripping section of the second distillation column has from 50 to 75% of the number of theoretical plates of this column.

7. The process according to claim 1, wherein a low boiler removal stage is carried out between the first and the second distillation stage, in which low boilers selected from a group consisting of methyl formate, methylal, dimethoxydimethyl ether and methanol are removed from the stream III.

8. The process according to claim 7, wherein the low boiler removal is carried out at a pressure of from 0.1 to 5.0 bar in a distillation column having at least 2 theoretical plates.

9. The process according to claim 1, characterized by the following composition of streams I-VII and X:
stream I: from 40 to 80% by weight of formaldehyde, from 20 to 59% by weight of water, from 1 to 30% by weight of trioxane;
stream II: from 55 to 85% by weight of formaldehyde, 15 to 45% by weight of water, 0 to 5% by weight of trioxane;
stream III: from 3 to 20% by weight of formaldehyde, 10 to 30% by weight of water, 60 to 75% by weight of trioxane;
stream IV: from 95 to 100% by weight of trioxane, 0 to 5% by weight of water and secondary components;
stream V: from 5 to 20% by weight of formaldehyde, 15 to 35% by weight of water, 50 to 75% by weight of trioxane;
stream VI: from 0 to 1% by weight of formaldehyde, 99 to 100% by weight of water;
stream VII: from 10 to 55% by weight of formaldehyde, 5 to 50% by weight of water, 5 to 55% by weight of trioxane,
stream X: from 10 to 50% by weight of formaldehyde, 10 to 50% by weight of water, 3 to 40% by weight of trioxane,
and the streams I, III, V and VII may also comprise up to 15% by weight of low boilers selected from the group consisting of methyl formate, methylal, dimethoxydimethyl ether and methanol.

10. A process for preparing trioxane from an aqueous formaldehyde solution, by feeding a stream XI of an aqueous formaldehyde of a trioxane synthesis stage and converting it under acidic conditions to obtain the stream I, and removing trioxane from the stream I by the process according to claim 1.

11. The process according to claim 10, wherein the stream XI is obtained from a stream VIII from an aqueous formaldehyde solution of low formaldehyde concentration by concentrating in an evaporator.

12. The process according to claim 11, wherein the stream IX is the formaldehyde-depleted vapor draw stream of the evaporator.

13. The process according to claim 1, wherein the bottom withdrawal stream II which is rich in formaldehyde and low in water is fed to a trioxane synthesis reactor together with the formaldehyde rich stream XI coming from an evaporator.

14. The process according to claim 1, wherein only small amounts of water are introduced into the second distillation stage, and only small amounts of water are separated off the top of the second distillation stage and recycled together with trioxane and formaldehyde to the first distillation stage.

15. The process according to claim 1, wherein the bottom withdrawal stream of the first distillation stage has a low water content, and the entire water content is separated off in the third distillation stage, and the stream X being a side withdrawal stream containing most of the water is generated in the first distillation stage and is directly passed into the third distillation stage.

16. The process according to claim 1, wherein the stream III is distilled in the second distillation stage after removing low boilers from stream III in a low boiler removal stage.

17. The process according to claim 1, wherein a stream IX which comprises water as the main component is fed with stream X into the third distillation stage.

* * * * *

UNITED STATES PATENT AND TRADEMARK OFFICE
CERTIFICATE OF CORRECTION

PATENT NO.        : 8,372,993 B2                                             Page 1 of 1
APPLICATION NO. : 12/523741
DATED             : February 12, 2013
INVENTOR(S)       : Lang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 694 days.

Signed and Sealed this
First Day of September, 2015

Michelle K. Lee
*Director of the United States Patent and Trademark Office*